United States Patent [19]

Nakata et al.

[11] Patent Number: 4,983,655

[45] Date of Patent: Jan. 8, 1991

[54] BLOCKED POLYISOCYANURATE COMPOUND AND PLASTISOL COMPOSITION CONTAINING SAME

[75] Inventors: Yoshihiro Nakata, Takatsuki; Tadao Kunishige, Kusatsu, both of Japan

[73] Assignee: Sunstar Giken Kabushiki Kaisha, Osaka, Japan

[21] Appl. No.: 370,790

[22] Filed: Jun. 23, 1989

[30] Foreign Application Priority Data

Jun. 24, 1988 [JP] Japan .............................. 63-157649
Jun. 25, 1988 [JP] Japan .............................. 63-157448

[51] Int. Cl.$^5$ .................. C08K 5/3462; C08G 18/28; C07D 251/00
[52] U.S. Cl. .................... 524/101; 524/507; 528/73; 544/222
[58] Field of Search ............... 524/507, 101; 528/73; 544/222

[56] References Cited

U.S. PATENT DOCUMENTS

| | | | |
|---|---|---|---|
| 4,260,541 | 4/1981 | Kolinsky et al. | 524/101 |
| 4,265,803 | 5/1981 | Soma et al. | 524/102 |
| 4,508,863 | 4/1985 | Kauder et al. | 524/101 |
| 4,605,596 | 8/1986 | Fry | 524/101 |
| 4,698,424 | 10/1987 | Engbert | 524/101 |
| 4,785,035 | 11/1988 | Pailuel et al. | 524/101 |
| 4,822,833 | 4/1989 | Zappia | 524/101 |

FOREIGN PATENT DOCUMENTS

| | | | |
|---|---|---|---|
| 0051239 | 5/1982 | European Pat. Off. | 544/222 |
| 0081142 | 6/1983 | European Pat. Off. | 544/222 |
| 3339579 | 5/1985 | Fed. Rep. of Germany | 544/222 |
| 48-26028 | 8/1973 | Japan | 544/222 |

*Primary Examiner*—Kriellion Morgan
*Attorney, Agent, or Firm*—Wegner, Cantor, Mueller & Player

[57] ABSTRACT

A plastisol composition comprising polyvinyl chloride as a main component, a plasticizer and a blocked compound of diisocyanate polymer with styrenated phenol as an adhesion-improver, and optionally a powdery curing agent having a melting point of 50° to 150° C. which is surface-treated, said composition having improved adhesion properties when gelated under low temperature conditions such as at 110° to 130° C. for 15 to 30 minutes and being useful as an adhesive, a sealant, or a coating agent, particularly as a sealant for the body of automobiles, and a novel blocked polyisocyanurate compound useful as an adhesion-improver for the above plastisol composition and also as an adhesive, a coating agent, a sealant, and an crosslinking agent for an active hydrogen-containing high molecular weight compound.

9 Claims, No Drawings

BLOCKED POLYISOCYANURATE COMPOUND AND PLASTISOL COMPOSITION CONTAINING SAME

The present invention relates to a plastisol composition comprising polyvinyl chloride as a main component, a plasticizer and a blocked compound of a diisocyanate polymer (i.e. polyisocyanurate) with styrenated phenol as an adhesion-improver, said plastisol composition being optionally supplemented with a powdery curing agent having a melting point of 50° to 150° C. which is surface-treated, and a novel blocked polyisocyanurate compound used therein as an adhesion-improver. The plastisol composition of the present invention has improved adhesion properties when gelated under low temperature conditions such as at 110° to 130° C. for 15 to 30 minutes.

TECHNICAL BACKGROUND AND PRIOR ART

A plastisol composition comprising polyvinyl chloride as a main component has been employed as adhesive, sealant or coating material in various fields. As such a type of plastisol composition, there is known, for example, a composition which comprises a polyvinyl chloride, a plasticizer and a blocked compound of a diisocyanate polymer with a long-chain alkylated phenol as an adhesion-improver (cf. Japanese Patent First Publication No. 41278/1987). This plastisol composition, however, has been found to have less adhesion properties under low temperature conditions such as 110° to 130° C., though it has an excellent storage stability under conditions of high temperature and high humidity without foaming and discoloration and is capable of forming a gelated compound with an excellent adhesion strength under high temperature conditions.

As an adhesion-improver, there are known some blocked polyisocyanurate compounds, including the above blocked compound of diisocyanate polymer with a long-chain alkylated phenol disclosed in Japanese Patent First Publication No. 41278/1987. Japanese Patent First Publication No. 53975/1987 further dicloses a blocked compound of diisocyanate polymer with an o-, m-, p-benzoic acid ester, which is used as coating agents, adhesives (or crosslinking agents therefor), or agents for modifying an active hydrogen-containing high molecular weight compound.

SUMMARY OF THE INVENTION

The present inventors have intensively studied to improve adhesion properties of the plastisol composition under low temperature conditions, and as a result, it was found that the adhesion properties under low temperature conditions can be remarkably improved by using a blocked compound of diisocyanate polymer (i.e. polyisocyanurate) with styrenated phenol as the adhesion-improver. That is, it has been found that when such a blocked isocyanurate compound is used as an adhesion-improver in the plastisol composition, the block thereof is easily removed under low temperature conditions so that the plastisol composition can easily be cured by water in the system or humidity in the air, and that the adhesion properties under low temperature can further be improved by adding a specific curing agent for an epoxy resin to the above plastisol composition.

An object of the present invention is to provide a plastisol composition having an improved adhesion under low temperature conditions which comprises a polyvinyl chloride, a plasticizer and a blocked compound of a diisocyanate polymer with styrenated phenol (i.e. a blocked polyisocyanurated polymer) as an adhesion-improver, which is useful as an adhesive, a sealant or a coating agent, particularly as a sealant for the body of automobiles. Another object of the present invention is to provide a plastisol composition having more improved adhesion under low temperature conditions which comprises a polyvinyl chloride, a plasticizer, a blocked polyisocyanurate compound as set forth above, and a powdery curing agent for an epoxy resin having a melting point of 50° to 150° C. which is surface-treated, which is useful for the same purpose as above. A further object of the present invention is to provide a blocked polyisocyanurate compound as set forth above which is useful as an adhesion-improver for the polyvinyl chloride plastisol composition and is also useful as an adhesive, a coating agent, a sealant, a crosslinking agent for an active hydrogen-containing high molecular weight compound. These and other objects and advantages of the invention will be apparent to those skilled in the art from the following description.

DETAILED DESCRIPTION OF THE INVENTION

One embodiment of the invention relates to a plastisol composition which comprises a polyvinyl chloride, a plasticizer and a blocked polyisocyanurate compound.

The polyvinyl chlorides used in the present invention may be those commonly used for a plastisol composition, including those prepared by polymerizing vinyl chloride alone or together with another copolymerizable monomer by emulsion polymerization, suspension polymerization, bulk polymerization, solution polymerization and the like. Such copolymerizable monomer includes, for example, vinyl esters of $(C_2-C_{10})$alkanoic acids (e.g. vinyl acetate, vinyl propionate, vinyl laurate, etc.), acrylic acid $(C_1-C_4)$alkyl esters (e.g. methyl acrylate, ethyl acrylate, butyl acrylate, etc.), methacrylic acid $(C_1-C_4)$alkyl esters (e.g. methyl methacrylate, ethyl methacrylate, etc.), maleic acid di$(C_1-C_4)$alkyl esters (e.g. dibutyl maleate, diethyl maleate, etc.), fumaric acid di$(C_1-C_4)$alkyl esters (e.g. dibutyl fumarate, diethyl fumarate, etc.), vinyl $(C_1-C_{10})$alkyl ethers (e.g. vinyl methyl ether, vinyl butyl ether, vinyl octyl ether, etc.), vinyl cyanates (e.g. acrylonitrile, methacrylonitrile, etc.), α-olefins (e.g. ethylene, propylene, styrene, etc.), vinyl halogenides or vinylidene halogenides other than vinyl chloride (e.g. vinylidene chloride, vinyl bromide, etc.), and the like.

The plasticizer used in the present invention may be those commonly used for plasticizing polyvinyl chloride and includes, but is not limited to, phthalic acid di$(C_4-C_{10})$alkyl or $(C_4-C_{10})$alkyl-$(C_6-C_8)$aryl or aralkyl esters such as di(n-butyl) phthalate, octyldecyl phthalate, diisodecyl phthalate, di(2-ethylhexyl) isophthalate, di(2-ethylhexyl) phthalate (DOP), butylbenzyl phthalate, dioctyl phthalate, dinonyl phthalate, diisononyl phthalate (DINP), diheptyl phthalate and butyl phthalyl butyl glycolate; aliphatic dibasic acid di$(C_4-C_{10})$alkyl esters such as dioctyl adipate, didecyl adipate, dioctyl sebacate, di(2-ethylhexyl) adipate, diisodecyl adipate, di(2-ethylhexyl) azelate, dibutyl sebacate and di(2-ethylhexyl) sebacate; phosphoric acid tri$(C_4-C_{10})$alkyl and/or $(C_6-C_8)$aryl esters such as tricresyl phosphate, trioctyl phosphate, tributyl phosphate, tri-2-ethylhexyl phosphate and 2-ethylhexyldiphenyl phosphate; epoxy type plasticizers such as epoxydized soybean oil and 2-ethylhexyl epoxidized tall oil fatty acid ester, and other polyester type plasticizers, which are used alone or in combination of at least two thereof. Such plasticizer has an influence on viscosity of the plastisol and properties of the gelated product, and may usually be used in an amount of 65–130 parts (parts by weight, hereinafter the same) per 100 parts of polyvinyl chloride.

The blocked polyisocyanurate compound of the present invention used as the adhesion-improver is a blocked compound of diisocyanate polymer with styrenated phenol. The blocked polyisocyanurate compound of the present invention is preferably a compound of the general formula (I):

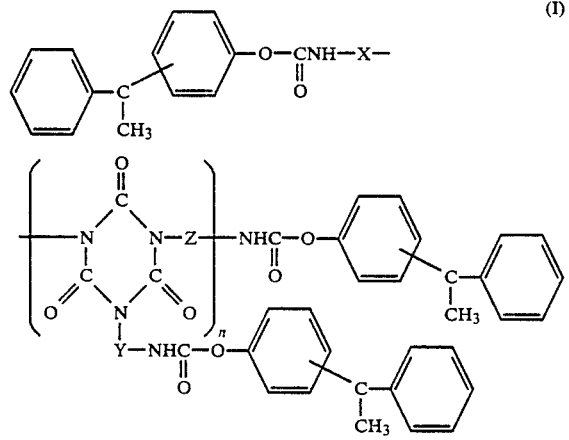

wherein X, Y and Z are the same or different and are each a tolylene diisocyanate moiety or a diphenylmethane diisocyanate moiety where NCO group is excluded, and n is an integer of 1 to 10.

The above blocked polyisocyanurate compound (I) is novel and can be prepared by the following process (a) or (b).

PROCESS (A)

A diisocyanate compound of the general formula (II):

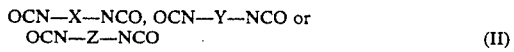

wherein X, Y and Z are the same as defined above, is subjected to an isocyanuration reaction to give a polyisocyanurate compound having the general formula (III):

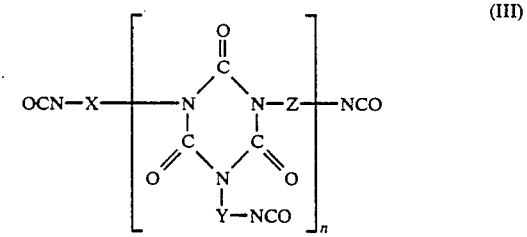

wherein X, Y, Z and n are the same as defined above.

The isocyanuration reaction is carried out by polymerizing the diisocyanate compound (II) in a suitable solvent such as acetic acid esters (e.g. ethyl acetate, methyl acetate, etc.), ketones (e.g. methyl ethyl ketone, methyl isobutyl ketone, etc.), phthalic acid esters (e.g. dibutyl phthalate, dioctyl phthalate, di(2-ethylhexyl) phthalate etc.), ethers (e.g. dioxane, tetrahydrofuran, etc.), aromatic hydrocarbons (e.g. toluene, xylene, etc.), dimethylformamide, N-methylpyrrolidone, and the like in the presence of a catalyst such as an alkali metal salt of an organic carboxylic acid (e.g. potassium acetate, sodium acetate, etc.), a tertiary amine compound, a quaternary ammonium compound, an epoxyamine compound, a phenolamine compound, and the like, at a temperature ranging from 20° to 80° C.

The starting diisocyanate compound (II) used in the above reaction includes tolylene diisocyanate (e.g. 2,4-tolylene diisocyanate, 2,6-tolylene diisocyanate) or diphenylmethane diisocyanate, which is used alone or in a mixture of two or three thereof.

The polyisocyanurate compound obtained above is then blocked by reacting with styrenated phenol of the formula (IV):

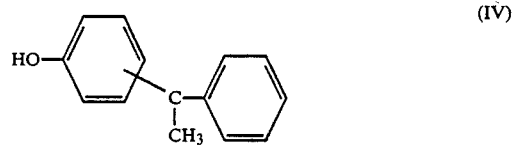

to prepare the blocked polyisocyanurate compound (I).

The blocking reaction is usually carried out in the presence of a reaction-accelerating catalyst such as an organic tin compound (e.g. dibutyl tin dilaurate, dioctyl tin dilaurate, stannous octoate, etc.), a metal salt of naphthenic acid (e.g. zinc naphthenate, cobalt naphthenate, etc.), iron acetylacetonate, manganese acetylacetonate, a tertiary amine compound, and the like, at a temperature ranging from 50° to 100° C.

PROCESS (B)

Alternatively, the diisocyanate compound (II) is firstly blocked with the styrenated phenol (IV) by reacting them at an NCO/OH equivalent ratio of 1.5 to 4, followed by subjecting the resultant to the isocyanuration reaction in the same manner as in the above process (a) to give the blocked polyisocyanurate compound (I). In this reaction, there are employed the same solvent and catalyst as in the process (a).

The present invention aims also to provide the above novel blocked polyisocyanurate compound (I), which is usually a pale yellow, clear viscous liquid and is useful as an adhesive, a coating agent, a sealant, or an agent for crosslinking an active hydrogen-containing high molecular weight compound, particularly as an adhesion-improver to be incorporated into a polyvinyl chloride plastisol composition suitable for sealing of the body of automobiles.

When the blocked polyisocyanurate compound (I) is used as an adhesion-improver for the plastisol composition of the invention, it may be used in an amount ranging from 3 to 30 parts, preferably from 5 to 20 parts per 100 parts of polyvinyl chloride. When the adhesion-improver is employed in an amount of less than 5 parts, the adhesion property of the obtained plastisol composition is insufficient, and when it is employed in an amount more than 30 parts, the physical property of the plastisol composition is deteriorated due to foaming.

In another embodiment of the invention, the plastisol composition comprising a polyvinyl chloride, a plasticizer and a blocked polyisocyanurate compound as mentioned above is supplemented with a powdery curing agent for an epoxy resin having a melting point of 50° to 150° C. which is surface-treated, by which the adhesion under low temperature conditions is more improved.

The powdery curing agent for an epoxy resin which is surface-treated (hereinafter referred to as "surface-treated curing agent") of the present invention is prepared by dispersing a powdery curing agent for an epoxy resin in a suitable insoluble medium and then adding a surface-treating agent thereto, or alternatively, by spraying a surface-treating agent on a powdery curing agent which is in a fluidized form in a gas stream.

The above powdery curing agent may be formed to have a suitable form by grinding a solid curing agent by conventional powdering procedures, for example, with hammer mill grinder, jet grinder, ball mill grinder, and is required to have a melting point of from 50° to 150° C., preferably from 60° to 120° C. When the melting point is below 50° C., the powdery curing agent may coagulate when stored, thereby making it difficult for handling, and when the melting point exceeds 150° C., the adhesion property of the obtained plastisol composition when gelated under low temperature conditions may be deteriorated.

The curing agent includes aromatic amines (e.g. meta-phenylenediamine, para-phenylenediamine, diaminodiphenylmethane, etc.); phthalic or succinic acid anhydrides having optionally a halogen or ($C_1$–$C_4$)alkyl substituent (e.g. phthalic anhydride, 3-chlorophthalic anhydride, 4-chlorophthalic anhydride, tetrahydrophthalic anhydride, dimethylsuccinic anhydride, etc.); imidazoles having optionally a ($C_1$–$C_{12}$)alkyl or phenyl substituent (e.g. imidazole, 2-methylimidazole, 2-undecylimidazole, 4-methylimidazole, 2-phenylimidazole, etc.) and the like. Further, the powdery curing agent includes the following group A compounds or reaction products of group A compounds and group B compounds.

[Group A compounds]: aliphatic polyamines such as ethylenediamine, diethylenetriamine, triethylenetetramine, tetraethylenepentamine and diethylaminopropylamine; aromatic polyamines such as diaminodiphenylsulfone and bis(aminomethyl)diphenylmethane; dibasic or tribasic carboxylic acid anhydrides such as trimellitic anhydride, pyromellitic anhydride, hexahydrophthalic anhydride and succinic anhydride; dibasic ($C_2$–$C_{10}$)carboxylic acid hydrazides such as adipic acid hydrazide, succinic acid hydrazide, sebacic acid hydrazide and terephthalic acid hydrazide; dicyandiamide; mono- or di-($C_1$–$C_{12}$)alkyl-substituted imidazoles such as 2-ethylimidazole, 2-isopropylimidazole, 2-dodecylimidazole and 2-ethyl-4-methylimidazole; carboxylic acid salts of the above imidazoles; and the like.

[Group B compounds]: dibasic ($C_2$–$C_{10}$) carboxylic acids such as succinic acid, adipic acid, sebacic acid, phthalic acid, terephthalic acid and dimer acid; ($C_1$–$C_4$)alkane- or ($C_6$–$C_8$)aryl-sulfonic acids such as ethanesulfonic acid and p-toluenesulfonic acid; isocyanates such as tolylene diisocyanate, 4,4'diphenyl diisocyanate and hexamethylene diisocyanate; p-hydroxystyrene resins; phenol resins; epoxy resins; and the like.

Among the above powdery curing agents having a melting point of 50° to 150° C., preferred ones are those containing at least two active hydrogens of amino group in a molecule [for example, the above aromatic amines; addition product of aliphatic polyamines (e.g. ethylenediamine, diethylenetriamine, triethylenetetramine, tetraethylenepentamine, hexamethylenediamine) with an epoxy resin; condensation products of an aliphatic polyamine and an aliphatic or aromatic dicarboxylic acid; polyureas such as a tolylenediisocyanate adduct of and hexamethylenediisocyanate adduct of an aliphatic amine; modified compounds of succinic acid hydrazide, adipic acid hydrazide and dicyandiamide], or those containing at least one tertiary amino group in a molecule [for example, the above imidazoles; adducts of a secondary amino group-containing compound (e.g. imidazoles, carboxylic acid salts of imidazoles, dimethylamine, diethylamine, dipropylamine, di(hydroxymethyl)amine, di(hydroxyethyl)amine) with an epoxy resin]. Preferable powdery curing agents in view of easiness of gelation and storage stability are imidazole derivatives containing at least one hydroxy group in a molecule [e.g. imidazoles having optionally a mono- or di-($C_1$–$C_{12}$)alkyl or phenyl substituent such as imidazole, 2-methylimidazole, 2-ethylimidazole, 2-ethyl-4-methylimidazole, 2-isopropylimidazole, 2-undecylimidazole and 2-phenylimidazole; adducts of a salt of the imidazoles with a carboxylic acid (e.g. acetic acid, lactic acid, salicylic acid, benzoic acid, adipic acid, phthalic acid, citric acid, tartaric acid, maleic acid, trimellitic acid) with an epoxy compound containing at least one epoxy group in a molecule (e.g. butyl glycidyl ether, hexyl glycidyl ether, phenyl glycidyl ether, p-xylyl glycidyl ether, glycidyl acetate, glycidyl butyrate, glycidyl hexoate, glycidyl benzoate)].

The surface-treating agent includes, for example, carboxylic acids such as ($C_1$–$C_4$)alkanoic acids (e.g. formic acid, acetic acid, propionic acid, butyric acid), dibasic ($C_2$–$C_8$)alkanoic acids (e.g. adipic acid, succinic acid), phenyl-dicarboxylic acids (e.g. phthalic acid, terephthalic acid); ($C_1$–$C_4$)alkane- or ($C_5$–$C_8$)aryl-sulfonic acids (e.g. ethanesulfonic acid, p-toluenesulfonic acid); isocyanates (e.g. phenyl isocyanate, 4.4'-diphenylmethane diisocyanate, tolylene diisocyanate, hexamethylene diisocyanate); ($C_2$–$C_4$)alkanoic or dibasic ($C_2$–$C_8$)alkanoic acid halides (e.g. acetyl chloride, propionic acid chloride, succinic acid chloride, adipic acid chloride); ($C_2$–$C_4$)alkanoic or phenyldicarboxylic acid anhydrides (e.g. acetic anhydride, propionic anhydride, phthalic anhydride); epoxy compounds containing at least one epoxy group; p-hydroxystyrene resins; phenol resins and the like, among which preferable ones are isocyanates containing at least one isocyanate group in a molecule, particularly tolylene diisocyanate and 4,4'-diphenylmethane diisocyanate.

The surface-treated curing agent thus prepared from the powdery curing agent and the surface-treating agent may be used in an amount ranging from 0.3 to 5 parts, preferably from 0.6 to 3 parts, per 100 parts of polyvinyl chloride resin. When the amount of the surface-treated curing agent is below 0.3 parts, the desired effect of improving adhesion properties at a lower temperature is not attained, and when the amount is over 5 parts, the adhesion properties at a lower temperature are no more improved but it is rather economically disadvantageous.

In place of a part of the surface-treated curing agent, the plastisol composition of the present invention may further contain a conventional latent curing agent for an epoxy resin (e.g. dicyandiamide, phthalic anhydride, trimellitic anhydride, tetrahydrophthalic anhydride, hexahydrophthalic anhydride, adipic acid dihydrazide, sebacic acid dihydrazide, isophthalic acid dihydrazide, terephthalic acid dihydrazide, diaminodiphenylsulfone, phenol resins, melamine resins, urea resins) to reduce the cost.

The plastisol composition of the present invention comprises the polyvinyl chloride, the plasticizer, the adhesion-improver [preferably the blocked polyisocyanurate compound (I)] and, optionally, the surface-treated curing agent (and optionally latent curing agent) in the above fixed ratio. The plastisol composition of the present invention may further contain conventional additives such as fillers (e.g. precipitated calcium carbonate which may be surface-treated with fatty acid or resin acid, heavy calcium carbonate, calcium oxide, clay, talc, silica, hollow glass powder, etc.), dehydrochlorination-inhibiting agents (e.g. metallic soap, an organic tin compound, etc.), heat stabilizers, pigments (e.g. titanium white, etc.), and the like.

The present invention is more specifically illustrated by the following Preparations, Examples and Comparative Examples but should not be construed to be limited thereto.

PREPARATION 1

To a solution of TDI-80 (tolylene diisocyanate as a mixture of 2,4-form 80% and 2,6-form 20%; 150 g) and di(2-ethylhexyl) phthalate (DOP; 750 g) are added styrenated phenol (100 g) and dibutyl tin dilaurate (0.5 g) and the reaction is carried out at 80° C. for 6 hours to give a partially blocked diisocyanate (free NCO group content: 5.1%). To this reaction mixture is added a 5% methanol solution (2 g) of isocyanuration catalyst (potassium acetate) and the reaction is continued at 80° C. until an absorption (2250 cm$^{-1}$) of NCO group disappears in IR. The obtained blocked polyisocyanurate compound has a regenerated NCO content of 8.4% and is confirmed by IR by absorption of an isocyanurate ring at 1410 cm$^{-1}$.

PREPARATION 2

To a solution of TDI-80 (150 g) and DOP (450 g) is added a 5% methanol solution (2 g) of potassium acetate and the reaction is carried out at 70° C. for 5 hours to give a polyisocyanurate compound (free NCO content: 4%). To this reaction solution are added styrenated phenol (130 g), DOP (390 g) and dibutyl tin dilaurate (0.5 g) and the reaction is conducted at 80° C. for 10 hours to give a blocked polyisocyanurate compound. It is confirmed by IR that this compound has no absorption (2250 cm$^{-1}$) of NCO group, and has regenerated NCO content: 8.8% and an absorption of an isocyanurate ring at 1410 cm$^{-1}$.

EXAMPLE 1 AND COMPARATIVE EXAMPLES 1–3

The components listed in the following Table 1 are mixed and dispersed and degassed in vacuum to prepare plastisol compositions. The obtained plastisol compositions are subjected to a measurement of viscosity (BH viscometer, 20° C.), a storage stability test by measuring a viscosity after storage at 40° C. for 7 days and the following test for adhesion properties at a lower temperature. Results are shown in Table 1.

TEST FOR ADHESION PROPERTIES AT A LOWER TEMPERATURE

Each composition prepared above was applied onto a cationic electro-deposition steel plate and the plate was heated at 120° C. for 30 minutes, followed by subjecting to peel test with nail to evaluate adhesion properties of each composition.

The evaluation was made in two-rank i.e.
o: excellent
x: wrong

TABLE 1

| Component | Ex. 1 | Comp. Ex. 1 | Comp. Ex. 2 | Comp. Ex. 3 |
|---|---|---|---|---|
| Polyvinyl chloride | 100 | 100 | 100 | 100 |
| DOP | 80 | 80 | 80 | 120 |
| Adhesion-improver A*[1] | 50 | — | — | — |
| Adhesion-improver B*[2] | — | 50 | — | — |
| Adhesion-improver C*[3] | — | — | 50 | — |
| Surface-treated calcium carbonate | 50 | 50 | 50 | 50 |
| Heavy calcium carbonate | 100 | 100 | 100 | 100 |
| Viscosity (cps) | 48000 | 60000 | 40000 | 33000 |
| Storage stability (40° C. × 7 days, cps) | 53000 | 70000 | Gelation | 38000 |
| Adhesion properties at lower temperature | o | x | o | x |

(Note) *[1]Blocked polyisocyanurate compound (I) obtained in Preparation 1 (solid content: 20%)
*[2]Blocked compound of tolylene diisocyanate polymer with methyl ethyl ketoxime (solid content: 20%, DOP solution)
*[3]20% DOP solution of tolylene diisocyante polymer

EXAMPLES 2–3 AND COMPARATIVE EXAMPLES 4–5

(1) Preparation of Plastisol Compositions

The components listed in the following Table 2 are mixed and dispersed and degassed in vacuum to prepare plastisol compositions.

(2) Test for Adhesion Properties as a Lower Temperature

Each composition prepared above was applied into a cationic electro-deposition steel plate and the plate was heated at 120° C. for 20 minutes, followed by subjecting to peel test with nail to evaluate adhesion properties of each composition.

The evaluation was made in two-rank i.e.
o: excellent
x: wrong

The results are shown in Table 2.

TABLE 2

| Component | Ex. 2 | Ex. 3 | Comp. Ex. 4 | Comp. Ex. 5 |
|---|---|---|---|---|
| Polyvinyl chloride*[4] | 60 | 60 | 60 | 60 |
| Polyvinyl chloride*[5] | 40 | 40 | 40 | 40 |
| DOP | 30 | 30 | 30 | 30 |
| Blocked isocyanate compound*[6] | 50 | 50 | 50 | 50 |
| Surface-treated curing agent*[7] | 2.4 | 0.6 | — | — |
| Latent curing agent*[8] | — | 2 | — | — |
| Surface-treated calcium carbonate*[9] | 25 | 25 | 25 | 35 |
| Hollow glass powder*[10] | 6 | 6 | 6 | — |
| Heavy calcium carbonate*[11] | — | — | — | 35 |
| Kerosine | 15 | 15 | 15 | 15 |
| Calcium oxide*[12] | 10 | 10 | 10 | 10 |
| Adhesion properties at a lower temp. | o | o | x | x |

(Note) *[4]Kaneka PCH-12Z (manufactured by Kanegahuchi Kagaku Kogyo Kabushiki Kaisha
*[5]Zeon G51 (manufactured by Nippon Zeon Co., Ltd., blended type)
*[6]Blocked polyisocyanurate comound (I) obtained in Preparation 1 (solid content: 20%)
*[7]Nobacure-3721 (manufactured by Asahi Chemical Industries, Co., Ltd.)
*[8]ADH (adipic acid dihydrazide) (manufactured by Nippon Hydrazine Industries Co., Ltd., used as a 50% solution in DINP)
*[9]Neolite SP (manufactured by Takehara Kgaku Co., Ltd.)
*[10]Glassballoon Z-37 (manufactured by Asahi Glass Co., Ltd., specific gravity: 0.36)
*[11]Whiton B (manufactured by Shiraishi Calucium Co., Ltd.)
*[12]QCX (manufactured by Inoue Sekkai Co., Ltd.)

What is claimed is:

1. A blocked polyisocyanurate compound of the general formula (I):

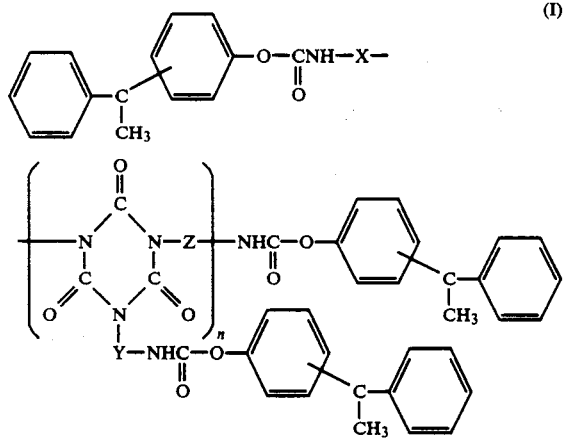

wherein X, Y and Z are the same or different and are each a tolylene diisocyanate moiety or a diphenylmethane diisocyanate moiety where all NCO groups are excluded, and n is an integer of 1 to 10.

2. A plastisol composition which comprises a polyvinyl chloride, a plasticizer and a blocked compound of a diisocyanate polymer with styrenated phenol as an adhesion-improver.

3. The plastisol composition of claim 2 wherein said blocked compound is the blocked polyisocyanurate compound as set forth in claim 1.

4. The plastisol composition of claim 3 wherein said blocked compound is the blocked polyisocyanurate compound as set forth in claim 1.

5. The plastisol composition of claim 2 which comprises 100 parts by weight of the polyvinyl chloride, 65 to 130 parts by weight of the plasticizer and 35 to 70 parts by weight of the blocked compound.

6. The plastisol composition of claim 5 which comprises 100 parts by weight of the polyvinyl chloride, 65 to 130 parts by weight of the plasticizer, 35 to 70 parts by weight of the blocked compound, and 0.3 to 5 parts by weight of the powdery curing agent.

7. A plastisol composition which comprises a polyvinyl chloride, a plasticizer, a blocked compound of a diisocyanate polymer with styrenated phenol as an adhesion-improver, and a powdery curing agent for an epoxy resin having a melting point of 50° to 150° C. which is surface-treated, wherein said powdery curing agent is a member selected from the group consisting of aromatic amines, phthalic or succinic acid anhydrides having optionally a halogen or ($C_1$–$C_4$) alkyl substituent and imidazoles having optionally a ($C_1$–$C_{12}$)alkyl or phenyl substituent.

8. A plastisol composition which comprises a polyvinyl chloride, a plasticizer, a blocked compound of a diisocyanate polymer with styrenated phenol as an adhesion improver, and a powdery curing agent for an epoxy resin having a melting point of 50° to 150° C. which is surface-treated, wherein said powdery curing agent is a member selected from the group A compounds or reaction products of group A compounds and group B compounds, wherein group A compounds represent aliphatic polyamines, aromatic polyamines, dibasic or tribasic carboxylic acid anhydrides, dibasic ($C_2$–$C_{10}$) carboxylic acid hydrazides, dicyandiamide, mono- or di-($C_1$–$C_{12}$)alkyl-substituted imidazoles, and carboxylic acid salts of the imidazoles, wherein group B compounds represent dibasic ($C_2$–$C_{10}$) carboxylic acids, ($C_1$–$C_4$)alkane- or ($C_6$–$C_8$)aryl-sulfonic acids, isocyanates, p-hydroxystyrene resin, phenol resin and epoxy resin.

9. The plastisol composition of claim 8 which comprises 100 parts by weight of the polyvinyl chloride, 65 to 130 parts by weight of the plasticizer, 35 to 70 parts by weight of the blocked compound, and 0.3 to 5 parts by weight of the powdery curing agent.

* * * * *